United States Patent
Wu et al.

(10) Patent No.: US 9,387,196 B2
(45) Date of Patent: Jul. 12, 2016

(54) 3-{1-[5-CHLORO-2-(2-ETHYLBUTOXY) BENZYL]-5-METHYL-1H-PYRAZOL-3-YL} PROPANOIC ACID IN CRYSTALLINE FORM AND METHODS FOR USE THEREOF

(71) Applicant: Allergan, Inc., Irvine, CA (US)

(72) Inventors: Ke Wu, Irvine, CA (US); Gyorgy F. Ambrus, Santa Ana, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/530,361

(22) Filed: Oct. 31, 2014

(65) Prior Publication Data

US 2015/0119438 A1  Apr. 30, 2015

Related U.S. Application Data

(60) Provisional application No. 61/898,181, filed on Oct. 31, 2013.

(51) Int. Cl.
*C07D 231/12* (2006.01)
*A61K 31/415* (2006.01)

(52) U.S. Cl.
CPC ............ *A61K 31/415* (2013.01); *C07D 231/12* (2013.01); *C07B 2200/13* (2013.01)

(58) Field of Classification Search
None
See application file for complete search history.

(56) References Cited

U.S. PATENT DOCUMENTS

| 6,511,999 B2 | 1/2003 | Burk et al. |
| 8,492,424 B2 | 7/2013 | Carling et al. |
| 2004/0162323 A1 | 8/2004 | Krauss et al. |

OTHER PUBLICATIONS

Caira, M.R., Crystalline Polymorphism of Organic Compounds, Topics in Current Chemistry 1998, 198: 164-208.
International Search Report and Written Opinion mailed on Jan. 16, 2015 for PCT/US2014/063557 filed on Oct. 31, 2014 in the name of Allergan, inc.

*Primary Examiner* — Kamal Saeed
(74) *Attorney, Agent, or Firm* — Jonathan Bass

(57) ABSTRACT

The present invention provides 3-{1-[5-chloro-2-(2-ethylbutoxy)benzyl]-5-methyl-1H-pyrazol-3-yl}propanoicacid in crystalline form. The present invention further provides methods for treating disorders associated with $DP_1$, FP, TP, $EP_1$ and $EP_4$ prostaglandin (PG) receptors.

18 Claims, 2 Drawing Sheets

3-{1-[5-CHLORO-2-(2-ETHYLBUTOXY) BENZYL]-5-METHYL-1H-PYRAZOL-3-YL} PROPANOIC ACID IN CRYSTALLINE FORM AND METHODS FOR USE THEREOF

CROSS-REFERENCE TO RELATED APPLICATIONS

This application is a non-provisional application claiming the benefit of U.S. provisional application 61/898,181 filed on Oct. 31, 2013 which is herein incorporated by reference in its entirety and serves as the basis for a priority claim of the present application.

FIELD

The present invention relates generally to 3-{1-[5-chloro-2-(2-ethylbutoxy) benzyl]-5-methyl-1H-pyrazol-3-yl}propanoic acid in crystalline form. The present invention further relates to methods for its preparation and to methods for treating disorders associated with the $DP_1$, FP, TP, $EP_1$ and $EP_4$ prostaglandin (PG) receptors.

BACKGROUND

The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion.

Prostaglandin $E_2$ ($PGE_2$) exerts allodynia through the $EP_1$ receptor subtype and hyperalgesia through $EP_2$ and $EP_3$ receptors in the mouse spinal cord. Furthermore, it has been shown that in the $EP_1$ knock-out mouse pain-sensitivity responses are reduced by approximately 50%. $EP_1$ receptor antagonist (ONO-8711) reduces hyperalgesia and allodynia in a rat model of chronic constriction injury and inhibits mechanical hyperalgesia in a rodent model of post-operative pain. The efficacy of $EP_1$ receptor antagonists in the treatment of visceral pain in a human model of hypersensitivity has been demonstrated. Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects. Moreover, as a result of sparing potentially beneficial prostaglandin pathways, these agents may have enhanced efficacy over NSAIDS and/or COX-2 inhibitors. (See Pub. No. US 2005/0065200 for other diseases that may be treated by EP4 receptor antagonists).

The TP (also known as $TxA_2$) receptor is a prostanoid receptor subtype stimulated by the endogenous mediator thromboxane. Activation of this receptor results in various physiological actions primarily incurred by its platelet aggregatory and smooth muscle constricting effects, thus opposing those of prostacyclin receptor activation.

TP receptors have been identified in human kidneys in the glomerulus and extraglomerular vascular tissue. Activation of TP receptors constricts glomerular capillaries and suppresses glomerular filtration rates indicating that TP receptor antagonists could be useful for renal dysfunction in glomerulonephritis, diabetes mellitus and sepsis.

Activation of TP receptors induces bronchoconstriction, an increase in microvascular permeability, formation of mucosal edema and mucus secretion, which are typical characteristic features of bronchial asthma. TP antagonists have been investigated as potential asthma treatments resulting in, for example, orally active Seratrodast (AA-2414). Ramatroban is another TP receptor antagonist currently undergoing phase III clinical trials as an anti-asthmatic compound.

Since the $DP_1$ receptor may trigger an asthmatic response in certain individuals, compounds that have $DP_1$ antagonist properties may be useful as anti-asthmatic drugs. (See Pub. No. 2004/0162323 for the disclosure of other diseases and conditions that may be treated with DP antagonists).

Finally, the FP receptor modulates intraocular pressure and mediates smooth muscle contraction of the sphincter muscles in the gastrointestinal tract and the uterus. Thus, antagonists of the FP receptor are useful for treating reproductive disorders. (See U.S. Pat. No. 6,511,999 for other diseases and conditions that may be treated with FP receptor antagonists).

It is known however that many drug compounds exist in one or more crystalline forms, referred to as polymorphs. These polymorphs of the same molecule exhibit different physical properties, such as melting point, solubility, hardness, etc. In such cases, the danger exists of less soluble polymorphic forms precipitating from a solution made from another more soluble but less stable form. The formation of crystals in an ophthalmic solution can cause serious injury to the eye. In addition, precipitation of the drug substance may cause an apparent reduction in potency and bioavailability of the product.

Accordingly, there is need for novel crystalline forms of compounds such as 3-{1-[5-chloro-2-(2-ethylbutoxy)benzyl]-5-methyl-1H-pyrazol-3-yl}propanoic acid.

SUMMARY

The invention provides 3-{1-[5-chloro-2-(2-ethylbutoxy) benzyl]-5-methyl-1H-pyrazol-3-yl}propanoic acid in crystalline form. The crystalline form of this compound is useful for treating a variety of disorders associated with $DP_1$, FP, TP, $EP_1$ and $EP_4$ prostaglandin (PG) receptors.

In one embodiment of the invention, there is provided 3-{1-[5-chloro-2-(2-ethylbutoxy)benzyl]-5-methyl-1H-pyrazol-3-yl}propanoic acid:

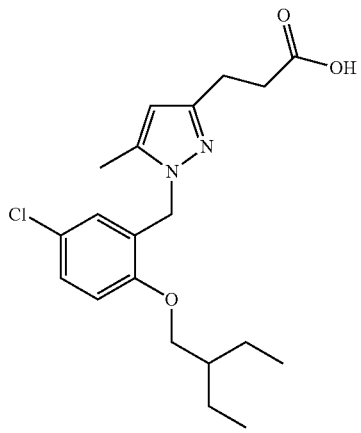 [SMILES: CCC(CC)COc1ccc(Cl)cc1Cn1nc(CCC(=O)O)cc1C]

in crystalline form.

In another embodiment of the invention, there are provided pharmaceutical compositions including a therapeutically effective amount of 3-{1-[5-chloro-2-(2-ethylbutoxy)benzyl]-5-methyl-1H-pyrazol-3-yl}propanoic acid in crystalline form in a pharmaceutically acceptable vehicle.

In another embodiment of the invention, there are provided methods for treating a disorder associated with $DP_1$, FP, $EP_1$, TP, and/or $EP_4$ receptors. Such methods can be performed, for example, by administering to a subject in need thereof a therapeutically effective amount of 3-{1-[5-chloro-2-(2-ethylbutoxy)benzyl]-5-methyl-1H-pyrazol-3-yl}propanoic acid in crystalline form.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation The present invention provides 3-{1-[5-chloro-2-(2-ethylbutoxy)benzyl]-5-methyl-1H-pyrazol-3-yl}propanoic acid:

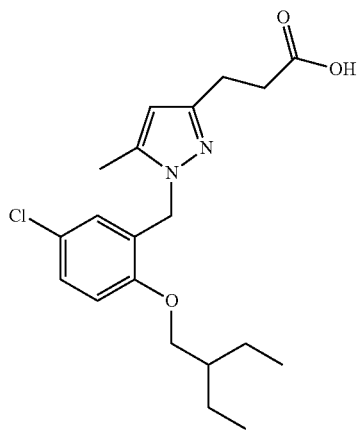 [SMILES: CCC(CC)COc1ccc(Cl)cc1Cn1nc(CCC(=O)O)cc1C]

in crystalline form.

Figure 1:
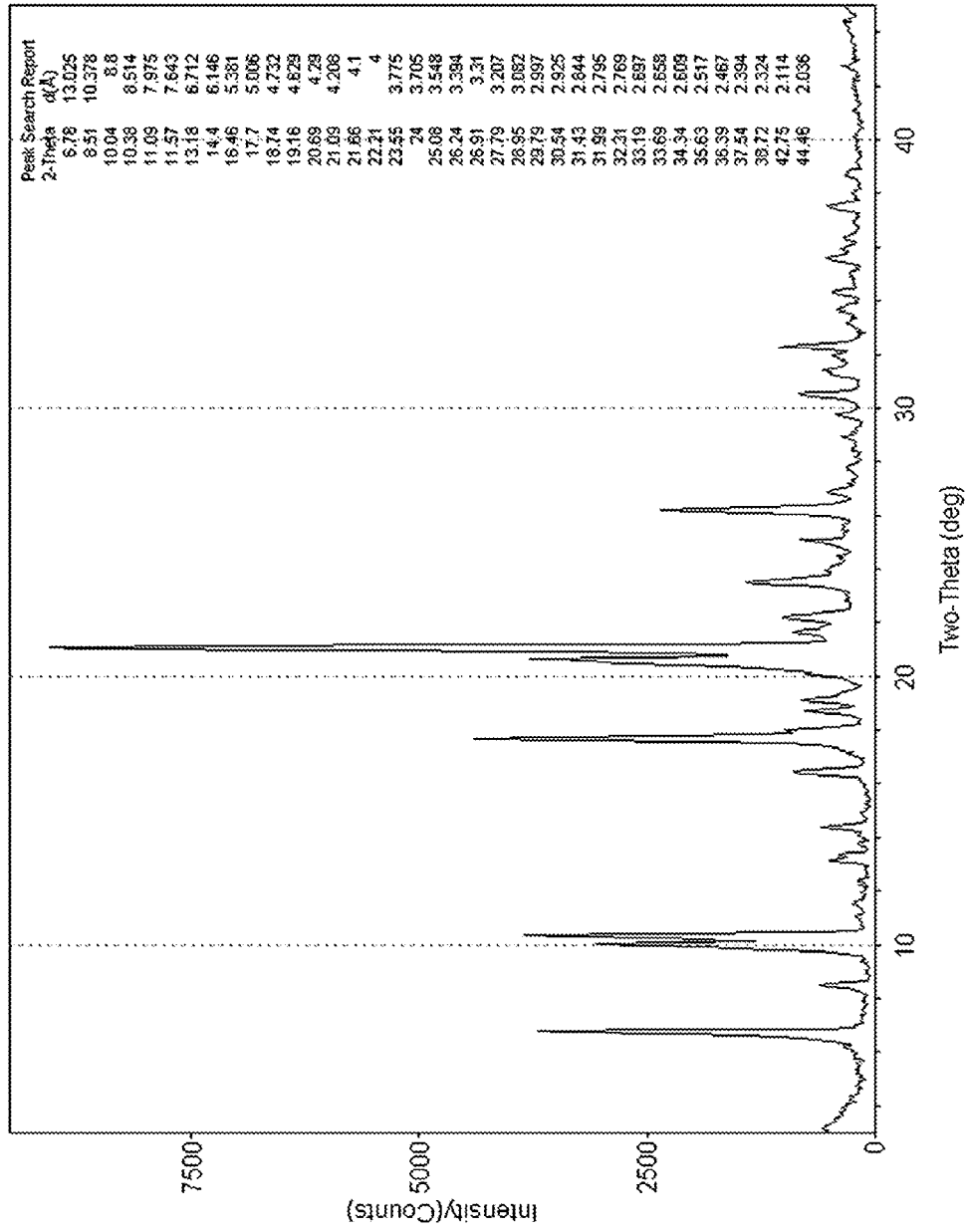
FIG. 1 illustrates a characteristic X-ray powder diffraction (XRPD) pattern of 3-{1-[5-chloro-2-(2-ethylbutoxy)benzyl]-5-methyl-1H-pyrazol-3-yl}propanoic acid in crystalline form.

In particular, the crystalline form described herein has an X-ray diffraction pattern (XRPD) substantially as shown in FIG. 1, including for example, peaks at about (2θ): 6.78, 10.38, 17.7, 20.69, 21.09, and 26.24. A skilled person would realize that, in general, the position of the 2θ peaks in an XRPD pattern can vary by approximately 0.1, and thus exemplary peaks of the crystal form herein described would appear at about (2θ) 6.78, 10.38, 17.7, 20.69, 21.09, and 26.24, wherein the term "about" indicates peaks at (2θ) 6.8±0.1, 10.4±0.1, 17.7±0.1, 20.7±0.1, 21.1±0.1, and 26.2±0.1 in an XRPD pattern. A skilled person would also understand that similar variations would apply to the other 2θ peaks in FIG. 1 which can also vary by approximately 0.1.

Figure 2:
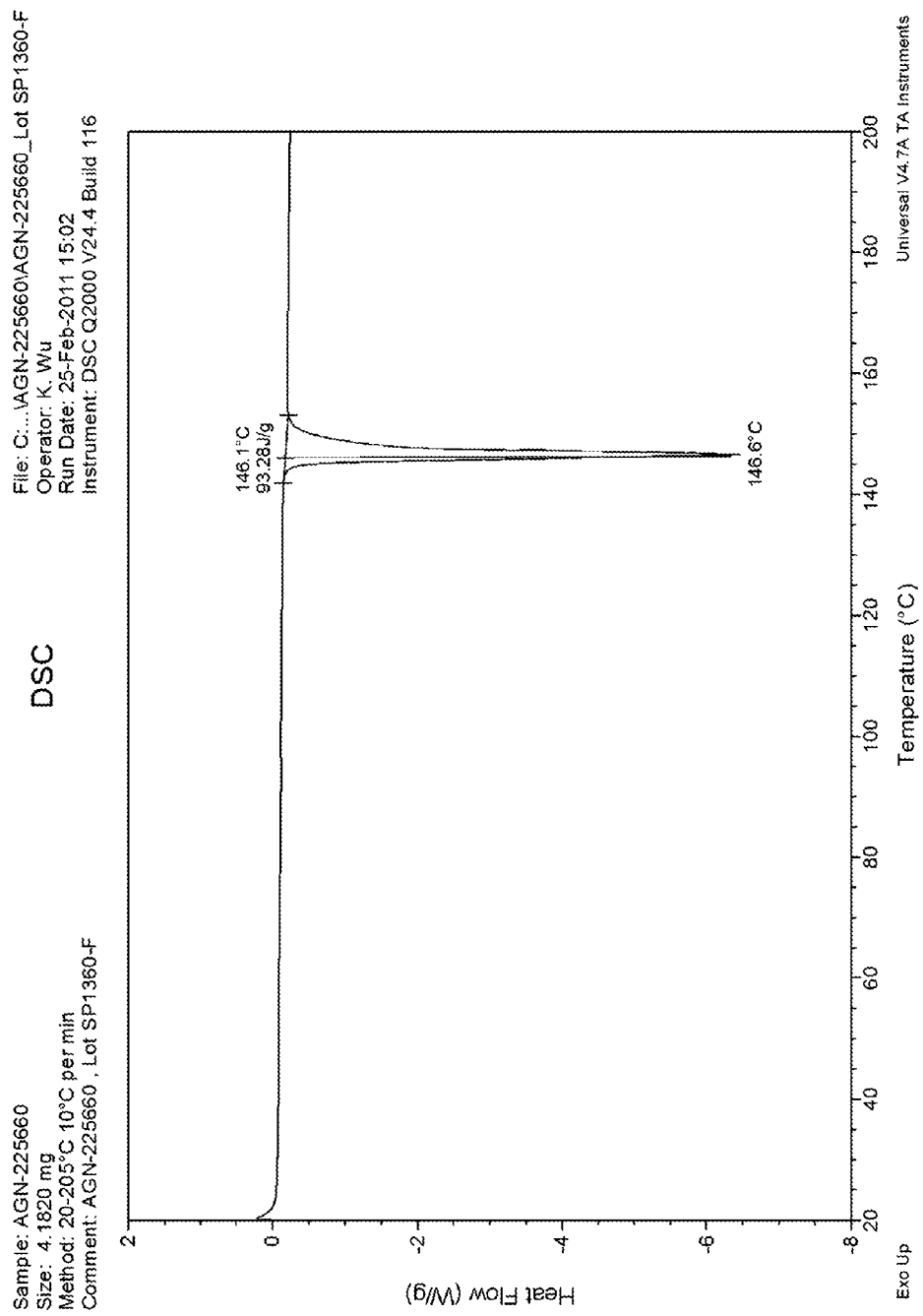
FIG. 2 illustrates a characteristic differential scanning calorimetry DSC profile of 3-{1-[5-chloro-2-(2-ethylbutoxy)benzyl]-5-methyl-1H-pyrazol-3-yl}propanoic acid, in crystalline form.

In addition, the crystalline form described herein has a differential scanning calorimetry profile as shown in FIG. 2, including having an endothermic onset at about 146.1° C. and a peak at 146.6° C. in its differential scanning calorimetry profile. This profile shows a single melting event indicating that Form I is essentially a pure crystal and does not contain any other crystalline forms. Accordingly, a skilled person would understand that the crystalline form described herein can be substantially free of other crystalline forms based on its DSC profile.

The crystalline form described herein can be made, for example, by methods described in Example 1 herein.

The crystalline form described herein may be administered to subjects in need thereof to treat disorders associated with DP1, FP, EP1, TP and/or EP4 receptors.

For example, the disorders may be related to inflammation, allergic conditions, asthma, allergic asthma, allergic rhinitis, uveitis and related disorders , atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, gangrene, glaucoma, hyperpyrexia, immune and autoimmune diseases, inflammatory conditions, metastatic tumor growth, migraine, mucus secretion disorders, nasal congestion, nasal inflammation, occlusive vascular diseases, ocular hypertension, ocular hypotension, osteoporosis, rheumatoid arthritis, pain, perennial rhinitis, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.

3-{1-[5-chloro-2-(2-ethylbutoxy)benzyl]-5-methyl-1H-pyrazol-3-yl}propanoic acid in crystalline form may be administered as a surgical adjunct in ophthalmology for cataract removal and artificial lens insertion, ocular implant procedures, photorefractive radial keratotomy and other ophthalmological laser procedures or as a surgical adjunct in a procedure involving skin incisions, relief of pain and inflammation and scar formation/keloids post-surgery, or for treating sports injuries and general aches and pains in muscles and joints.

In some embodiments the disorder associated with $DP_1$, FP, $EP_1$, TP, and/or $EP_4$ receptors is a disorder associated with $EP_1$ and/or $EP_4$ receptors.

In some embodiments the disorder associated with $DP_1$, FP, $EP_1$, TP, and/or $EP_4$ receptors is an allergic condition, e.g. a dermatological allergy, or an ocular allergy, or a respiratory allergy, e.g. nasal congestion, rhinitis, and asthma.

In some embodiments the disorder associated with $DP_1$, FP, $EP_1$, TP, and/or $EP_4$ receptors is pain. Such as pain associated with arthritis, migraine, or headache, or ocular pain or post-surgical ocular pain.

In some embodiments the disorder associated with $DP_1$, FP, $EP_1$, TP, and/or $EP_4$ receptors is associated with the gastrointestinal tract, wherein said condition or disease may be peptic ulcer, heartburn, reflux esophagitis, erosive esophagitis, non-ulcer dyspepsia, infection by *Helicobacter pylori*, alrynitis, and irritable bowel syndrome.

In some embodiments the disorder associated with $DP_1$, FP, $EP_1$, TP, and/or $EP_4$ receptors is ocular hypertension and/or glaucoma.

In some embodiments the disorder associated with $DP_1$, FP, $EP_1$, TP, and/or $EP_4$ receptors is may relate to surgical procedures to treat pain, inflammation and other unwanted sequelae wherein the surgical procedure includes incision, laser surgery or implantation.

In some embodiments the disorder associated with $DP_1$, FP, $EP_1$, TP, and/or $EP_4$ receptors is related to pain and inflammation and post-surgical scar and keloid formation For ophthalmic pharmaceutical compositions, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/w) |
| --- | --- |
| active ingredient | about 0.001-5 |
| preservative | 0 to 0.10 |
| vehicle | 0 to 40 |
| tonicity adjuster | 0 to 10 |
| buffer | 0.01 to 10 |
| pH adjuster | q.s. pH 4.5 to 7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five unit doses, where a typical unit dose is from one to about 8 drops, preferably one to about 3 drops. The volume of one drop usually is about 20-35 µl.

The following examples are intended only to illustrate the present invention and should in no way be construed as limiting the subject invention.

EXAMPLES

X-Ray powder diffraction patterns (XRPD) were obtained for the crystalline form described herein under the following conditions:

Equipment: Rigaku Miniflex

Scan range: 5 to 45° (2θ)

Scan speed: 2° (2θ) per minute

Step width: 0.05° (2θ)

X-ray information: Cu Kα, λ=1.54 Å, 30 kV/15 mA

Approximately 3-5 mg of the sample was gently applied on a zero background sample holder and subjected to XRPD scanning.

Differential scanning calorimetry was performed by loading 4 to 5 mg material in a nonhermetic DSC sample pan and then subjecting the sample to a heat ramp from 20 to 205° C. at a rate of 10° C. per min.

The crystal form described herein was obtained via a 3-day solvent/anti-solvent assessment protocol as set forth in Table 1. Amorphous 3-{1-[5-chloro-2-(2-ethylbutoxy)benzyl]-5-methyl-1H-pyrazol-3-yl}propanoic acid can be prepared according to the procedure set forth in U.S. Pat. No. 8,492,424.

In particular, the protocols of Table 1 were performed as follows: an amount of approximately 20 to 50 mg drug substance (see $WT_{API}$ in Table 1) was mixed with appropriate volume (see V solvent 1 and V solvent 2 in Table 1) of pre-defined solvent or solvent mixture (solvent+antisolvent) in a glass vial. Next, the sample vial was subjected to temperature cycling between 20° C. and 50° C. at 0.1° C./min under magnetic stirring at 700 rpm. At the end of each heating or cooling step, the samples were maintained isothermal for at least 300 minutes to allow temperature equilibrium or crystal growth. Generally, at least three heat-cool-heat cycles were performed. At the end of the thermo-cycling, the solids were isolated by filtration. The 16 labeled protocols in Table 1 provided the crystalline form described herein.

TABLE 1

Polymorph screening on 3-{1-[5-chloro-2-(2-ethylbutoxy)benzyl]-5-methyl-
1H-pyrazol-3-yl}propanoic acid, by maturation (RT to 50° C.)

| Label | Solvent | Wt$_{API}$ (mg) | Antisolvent | Observation before AS | V solvent 1 (µL) | V solvent 2 (µL) |
|---|---|---|---|---|---|---|
| 1 | diethyl ether | 38.4 | n/a | white suspension | 200 | 0 |
| 2 | iPrOAc | 28.5 | n/a | white suspension | 200 | 0 |
| 3 | acetone | 39.4 | n/a | white suspension | 100 | 0 |
| 4 | methanol | 44.9 | n/a | white suspension | 100 | 0 |
| 5 | THF | 28.4 | H$_2$O | clear | 100 | 500 |
| 6 | EtOAc | 30.1 | n/a | white suspension | 200 | 0 |
| 7 | ethanol | 34.4 | n/a | white suspension | 100 | 0 |
| 8 | acetonitrile | 23.2 | n/a | white suspension | 200 | 0 |
| 9 | 2-propanol | 24.0 | n/a | white suspension | 200 | 0 |
| 10 | 1-BuOH (:H2O) | 22.4 | n/a | white suspension | 200 | 0 |
| 11 | water | 25.1 | n/a | white suspension | 200 | 0 |
| 12 | nitromethane | 27.5 | DCM | white suspension | 100 | 100 |
| 13 | 1,4-dioxane | 23.6 | H$_2$O | clear | 100 | 300 |
| 14 | MIBK | 22.9 | n/a | white suspension | 200 | 0 |
| 15 | Anisole | 27.2 | n/a | white suspension | 200 | 0 |
| 16 | NMP | 22.6 | H$_2$O | clear | 100 | 200 |

The assessment protocol summarized in Table 1 was performed in order to discover the existence of different polymorphs or forms of 3-{1-[5-chloro-2-(2-ethylbutoxy)benzyl]-5-methyl-1H-pyrazol-3-yl}propanoic acid. A single crystalline solid form of this compound of a unique crystalline character was identified. FIG. 1 shows that the powder X-ray diffractogram for the compound is characteristic of a crystalline solid as evidenced by the numerous sharp reflection peaks. This solid form (a.k.a. Form I) has a melting endotherm onset at 146.1° C. (ΔH=93 J/g) as shown in the differential scanning profile in FIG. 2. This profile shows a single melting event indicating that Form 1 is essentially a pure crystal and does not contain any other crystalline forms.

While this invention has been described with respect to these specific examples, it is understood that other modifications and variations are possible without departing from the spirit of the invention as would be understood to a skilled person upon a reading of the present disclosure.

What is claimed is:

1. A crystalline form of 3-{1-[5-chloro-2-(2-ethylbutoxy)benzyl]-5-methyl-1H-pyrazol-3-yl}propanoic acid.

2. The crystalline form of claim 1, having an X-ray powder diffraction pattern with peaks at about (2θ): 6.78, 10.38, 17.7, 20.69, 21.09, and 26.24.

3. The crystalline form of claim 1 having the X-ray diffraction pattern substantially as shown in FIG. 1.

4. The crystalline form of claim 1 having an endothermic onset at about 146.1° C. and a peak at 146.6° C. in its differential scanning calorimetry profile.

5. The crystalline form of claim 1 having the differential scanning calorimetry profile as shown in FIG. 2.

6. A pharmaceutical composition comprising a therapeutically effective amount of the crystalline form of claim 1 in a pharmaceutically acceptable vehicle.

7. A method for treating a disorder associated with DP$_1$, FP, EP$_1$, TP, and/or EP$_4$ receptors comprising administering to a subject in need thereof a therapeutically effective amount the crystalline form of claim 1.

8. The method of claim 7 wherein the disorder is an allergic condition.

9. The method of claim 8 wherein the allergic condition is a dermatological allergy, an ocular allergy, or a respiratory allergy.

10. The method of claim 7 wherein the disorder is pain.

11. The method of claim 10 wherein the pain is arthritis pain, headache pain, or ocular pain.

12. The method of claim 11 wherein the pain is migraine pain.

13. The method of claim 11 wherein the pain is post-surgical ocular pain.

14. The method of claim 7 wherein the disorder is associated with the gastrointestinal tract.

15. The method of claim 14 wherein the disorder is peptic ulcer, heartburn, reflux esophagitis, erosive esophagitis, non-ulcer dyspepsia, infection by *Helicobacter pylori*, alrynitis, or irritable bowel syndrome.

16. The method of claim 7 wherein the disorder is ocular hypertension.

17. The method of claim 16 wherein the disorder is glaucoma.

18. The crystalline form of claim 1 substantially free of other crystalline forms.

* * * * *